(12) United States Patent
Alla et al.

(10) Patent No.: US 10,450,315 B2
(45) Date of Patent: Oct. 22, 2019

(54) PROCESS FOR THE PREPARATION OF DIPEPTIDYL PEPTIDASE-4 (DPP-4) ENZYME INHIBITOR

(71) Applicants: Lee Pharma Limited, Hyderabad (IN); Venkat Reddy Alla, Hyderabad (IN); Raghumitra Alla, Hyderabad (IN); Srinivas Reddy Mallepalli, Hyderabad (IN); Suresh Babu Nandam, Hyderabad (IN); Madhukar Reddy Guda, Hyderabad (IN); Raja Reddy Alluri, Hyderabad (IN)

(72) Inventors: Venkat Reddy Alla, Hyderabad (IN); Raghumitra Alla, Hyderabad (IN); Srinivas Reddy Mallepalli, Hyderabad (IN); Suresh Babu Nandam, Hyderabad (IN); Madhukar Reddy Guda, Hyderabad (IN); Raja Reddy Alluri, Hyderabad (IN)

(73) Assignee: Lee Pharma Limited (IN)

( * ) Notice: Subject to any disclaimer, the term of this patent is extended or adjusted under 35 U.S.C. 154(b) by 0 days.

(21) Appl. No.: 15/542,093

(22) PCT Filed: Feb. 20, 2015

(86) PCT No.: PCT/IB2015/051312
§ 371 (c)(1),
(2) Date: Jul. 7, 2017

(87) PCT Pub. No.: WO2016/110750
PCT Pub. Date: Jul. 14, 2016

(65) Prior Publication Data
US 2018/0265513 A1  Sep. 20, 2018

(30) Foreign Application Priority Data
Jan. 8, 2015 (IN) .............................. 138/CHE/2015

(51) Int. Cl.
*C07D 487/04* (2006.01)
*C07C 233/05* (2006.01)

(52) U.S. Cl.
CPC .......... *C07D 487/04* (2013.01); *C07C 233/05* (2013.01); *C07B 2200/07* (2013.01); *C07B 2200/13* (2013.01)

(58) Field of Classification Search
CPC .............. C07D 487/04; C07B 2200/13; C07B 2200/07; C07C 233/05
See application file for complete search history.

(56) References Cited

U.S. PATENT DOCUMENTS

| 5,616,793 A | 4/1997 | Huckabee et al. |
| 7,326,708 B2 | 2/2008 | Cypes et al. |
| 8,476,437 B2 | 7/2013 | Kothari et al. |

FOREIGN PATENT DOCUMENTS

| WO | 2003004498 | 1/2003 |
| WO | 2004085661 | 10/2004 |
| WO | 2004087650 | 10/2004 |
| WO | 2009084024 | 7/2009 |
| WO | 2009084024 A2 * | 7/2009 |
| WO | 2009085990 | 7/2009 |
| WO | 2010122578 | * 10/2010 |

OTHER PUBLICATIONS

International Search Report and Written Opinion for PCT Application No. PCT/IB2015/051312 dated Dec. 17, 2015 (10 pages).

* cited by examiner

*Primary Examiner* — Alexander R Pagano
*Assistant Examiner* — Ebenezer O Sackey
(74) *Attorney, Agent, or Firm* — Shumaker & Sieffert, P.A.

(57) ABSTRACT

The present invention relates to a novel and improved process for the preparation of Sitagliptin of Formula (I) and its pharmaceutically acceptable salts. The present invention also relates to novel intermediates and process for the preparation of intermediates used in the preparation of Sitagliptin.

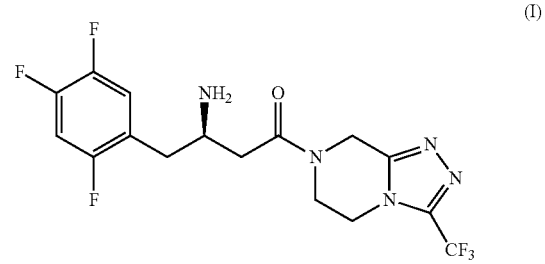

(I)

16 Claims, 3 Drawing Sheets

PROCESS FOR THE PREPARATION OF DIPEPTIDYL PEPTIDASE-4 (DPP-4) ENZYME INHIBITOR

FIELD OF THE INVENTION

The present invention provides a novel and improved process for the preparation of Sitagliptin of Formula I and its pharmaceutically acceptable salts.

Formula I

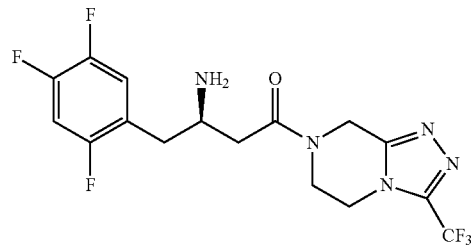

The present invention also provides novel intermediates and process for the preparation of intermediates used in the preparation of Sitagliptin.

BACKGROUND OF THE INVENTION

Sitagliptin phosphate is glucagen like peptide 1 metabolism modulator, hypoglycemic agent and dipeptidyl peptidase IV inhibitor. Sitagliptin phosphate is currently marketed in the under the trade name of JANUVIA® in its monohydrate form. JANUVIA® is indicated to improve glycemic control in patients with type 2 diabetes mellitus. Its chemical name is 7-[(3R)-3-amino-1-oxo-4-(2,4,5-trifluorophenyl)butyl]5,6,7,8-tetrahydro-3-(trifluoromethyl)-1,2,4-triazolo[4,3,-a]pyrazine phosphate monohydrate and the molecular Formula is $C_{16}H_{15}F_6N_5O \cdot H_3PO_4 \cdot H_2O$ with a molecular weight of 523.32. The structural Formula of Sitagliptin phosphate monohydrate is:

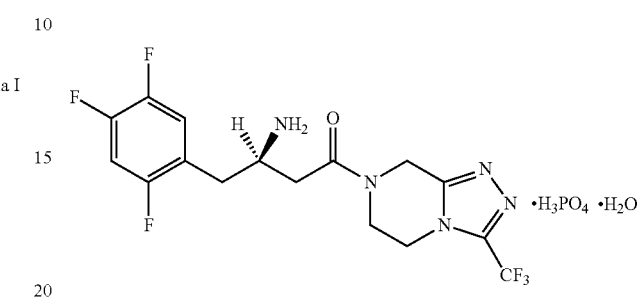

PCT Publication No. WO 03/004498 assigned to Merck & Co., describes a class of beta-amino tetrahydro triazolo[4,3-a]pyrazines, which are potent inhibitors of DP-IV and therefore useful for the treatment of Type 2 diabetes. Specifically disclosed in WO 03/004498 is 7-[(3R)-3-amino-4-(2,4,5-trifluorophenyl)butanoyl]-3-(trifluoromethyl)-5,6,7,8-tetrahydro-1,2,4-triazolo[4,3-α]pyrazine hydrochloride. This application also discloses a method of introducing a chiral amine group using a chiral pyrazine derivative and to prepare Sitagliptin by Arndt-Eistert Homologation using t-butyloxycarbonylamino-4-(2,4,5-trifluorophenyl)-butyric acid. The process is shown in the scheme given below:

Scheme I

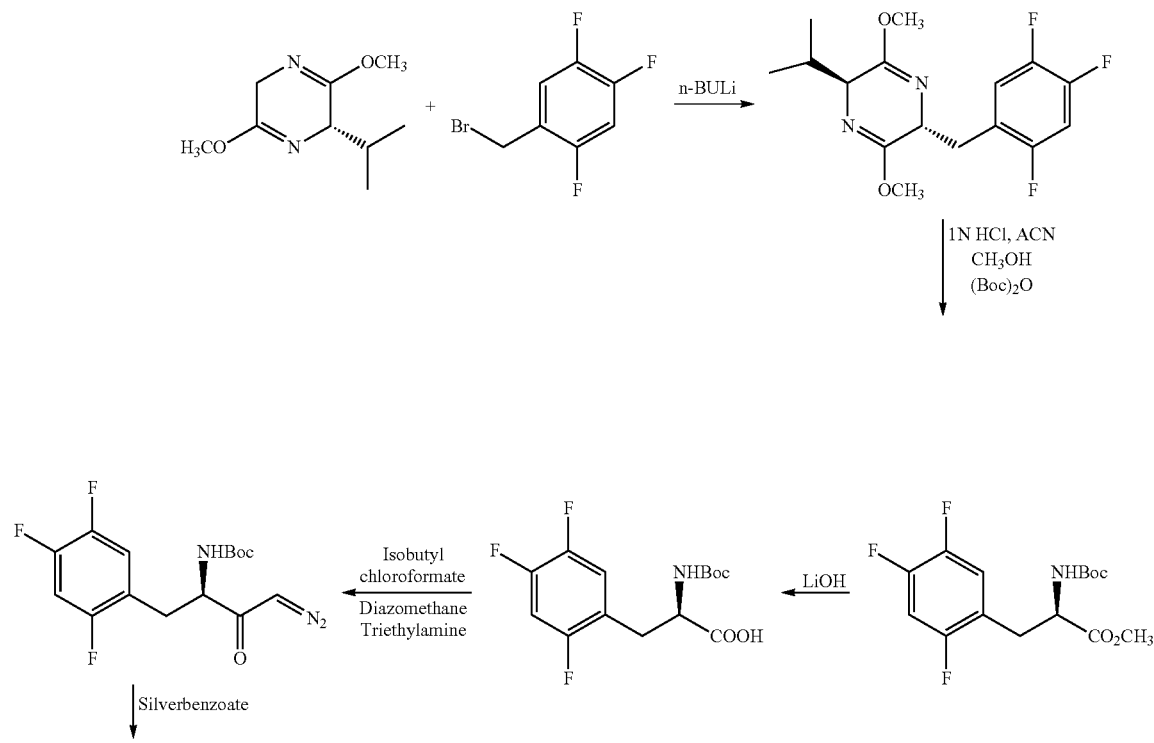

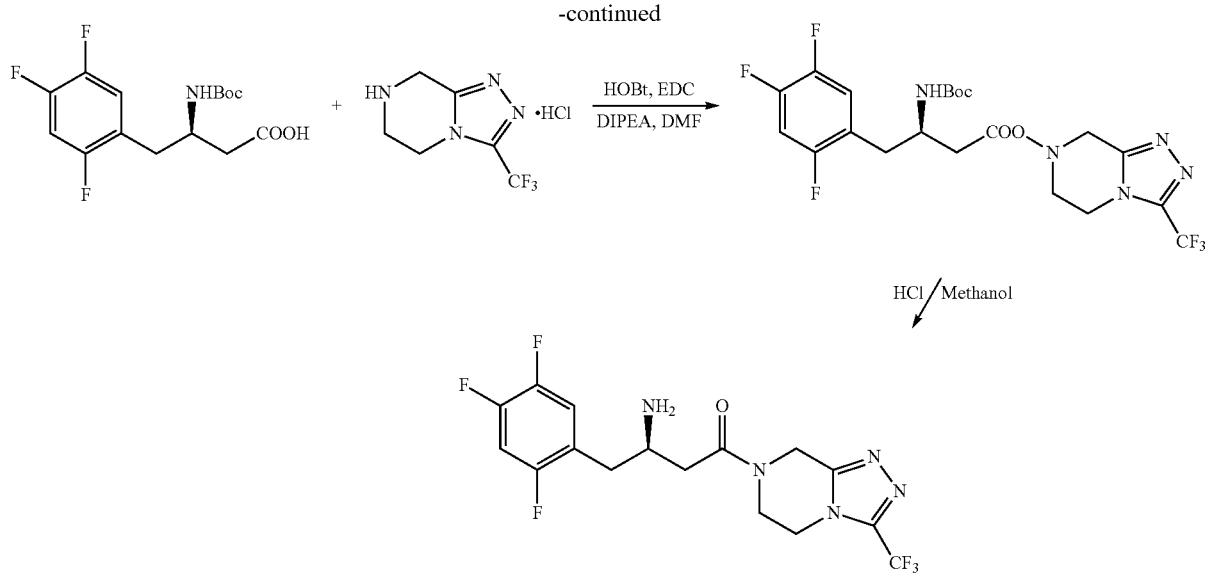

Formula I wherein,
Boc is tert-butyloxycarbonyl,
TEA is trimethylamine
HOBt is 1-Hydroxybenzotriazole,
EDC is 1-Ethyl-3-(3-dimethylaminopropyl) carbodiimide
DIPEA is N,N-diisopropylethylamine PCT publication No. WO 2004/087650 discloses the synthesis of Sitagliptin via the stereoselective reduction of methyl 4-(2,4,5-trifluorophenyl)-3-oxobutanoate to produce the Sitagliptin intermediate (S)-methyl-4-(2,4,5-trifluorophenyl)-3-hydroxybutanoate. The said stereoselective reduction is performed by hydrogenation with $H_2$ and (S)-BINAP-RuCl$_2$ catalyst in presence of hydrochloric acid followed by inversion of stereochemical centre achieved by Mitsunobu cyclization of (3S)—N-benzyloxy-3-hydroxy-4-(2,4,5-trifluorophenyl)butyramide. The process is illustrated in the scheme given below:

Scheme II

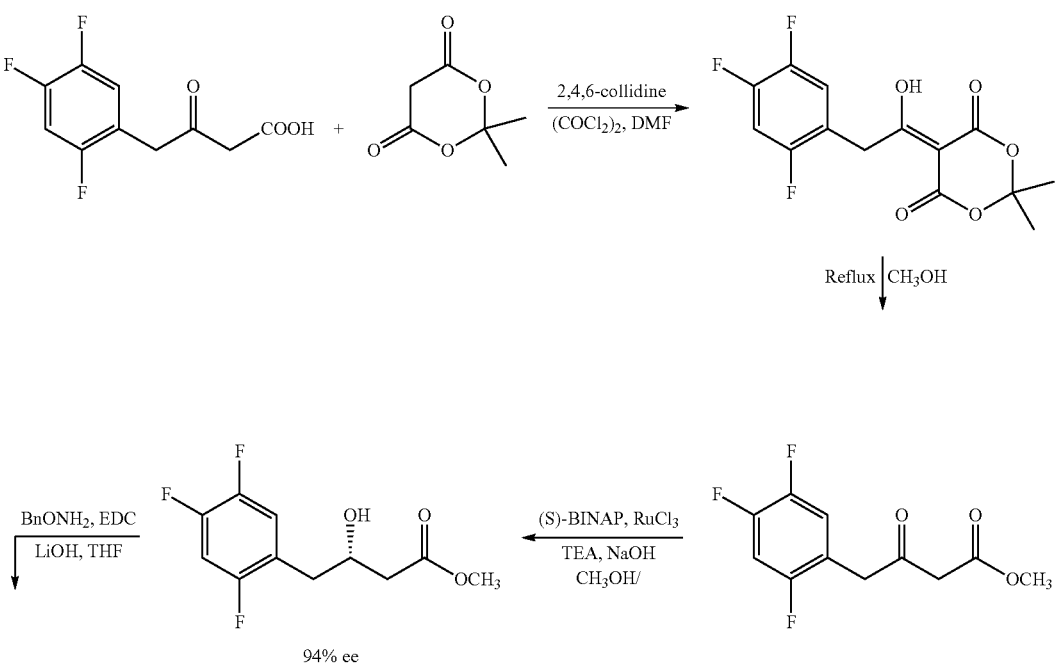

94% ee

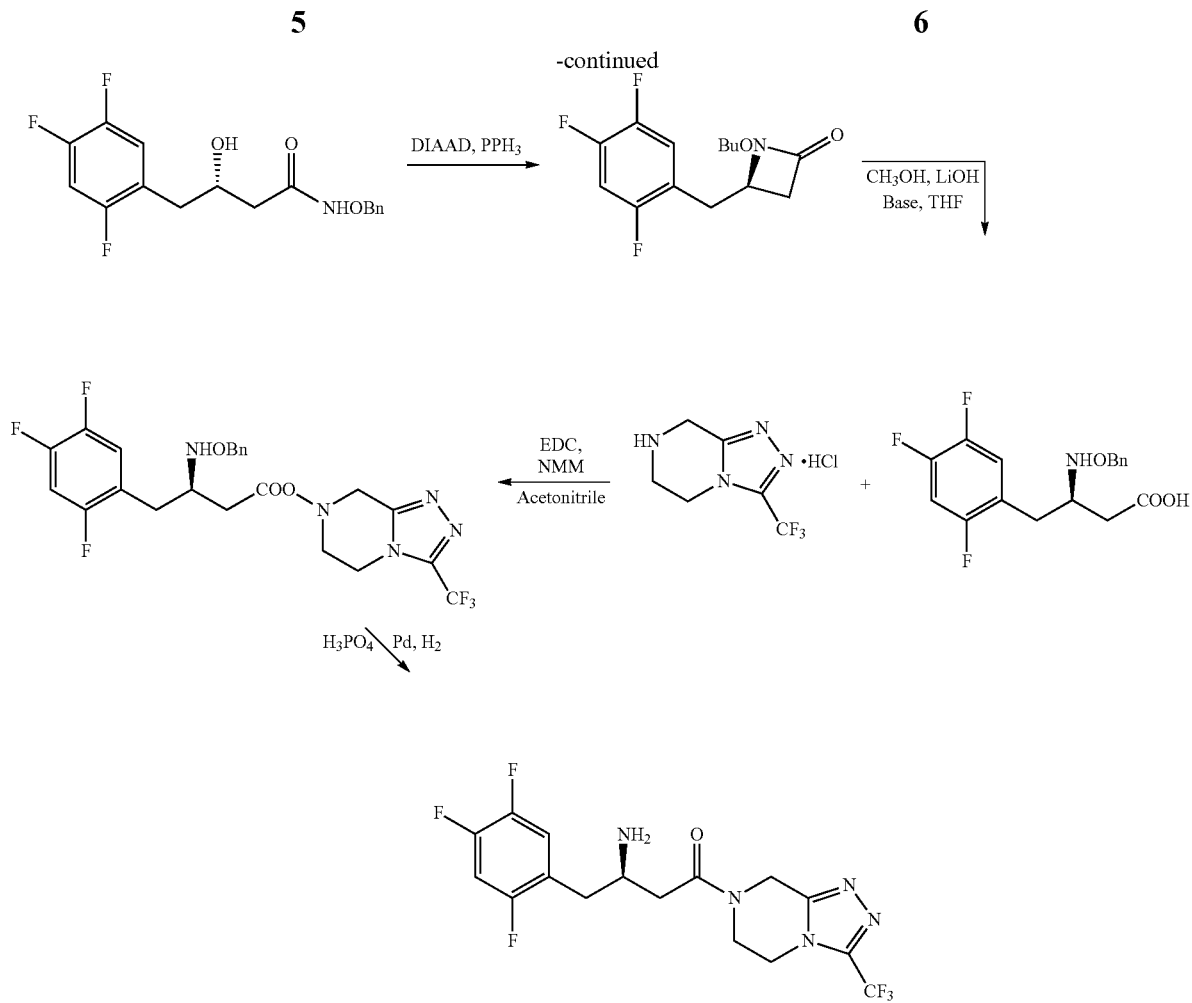
Wherein
BINAP is 2,2'-bis(diphenylphosphino)-1,1'-binaaphthyl,
EDC is 1-Ethyl-3-(3-dimethylaminopropyl)carbodiimide
Bn is benzyl,
DIAD is diisopropylazodicarboxylate,
NMM is N-methylmorpholine,
PCT publication No. WO 2004/085661 discloses a process for the preparation of Sitagliptin by reduction of a substituted enamine. The process is shown in the scheme given below:
Scheme II
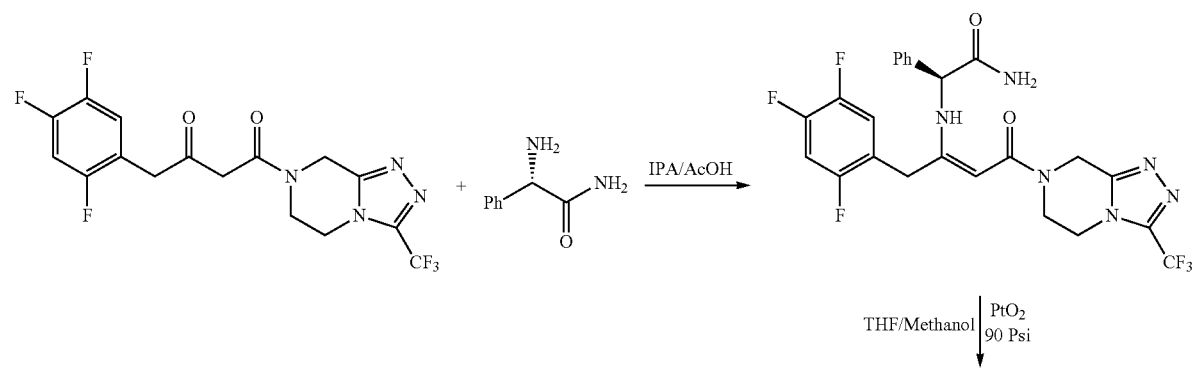

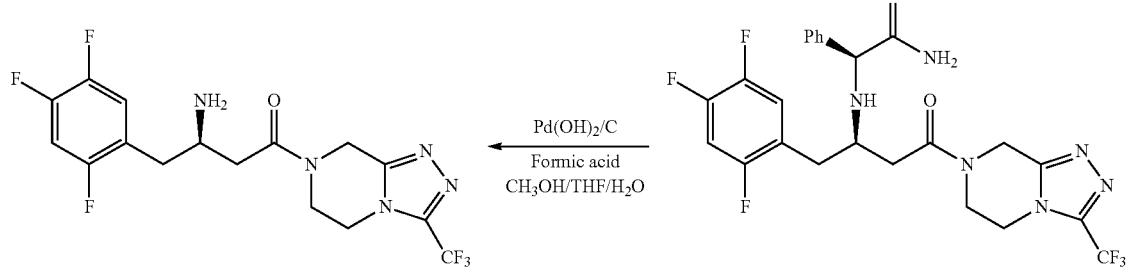

PCT publication No. WO 2009/084024 discloses process for the preparation of Sitagliptin and its pharmaceutically acceptable salts by resolving the amine with a resolving agent. Most of the time the said patent application describes the resolving agent as dibenzyl-L-tartaric acid. The said patent describes that the chiral purity obtained is only 85-90% that too after repeated recrystallizations. The process is shown in the scheme given below:

Scheme III

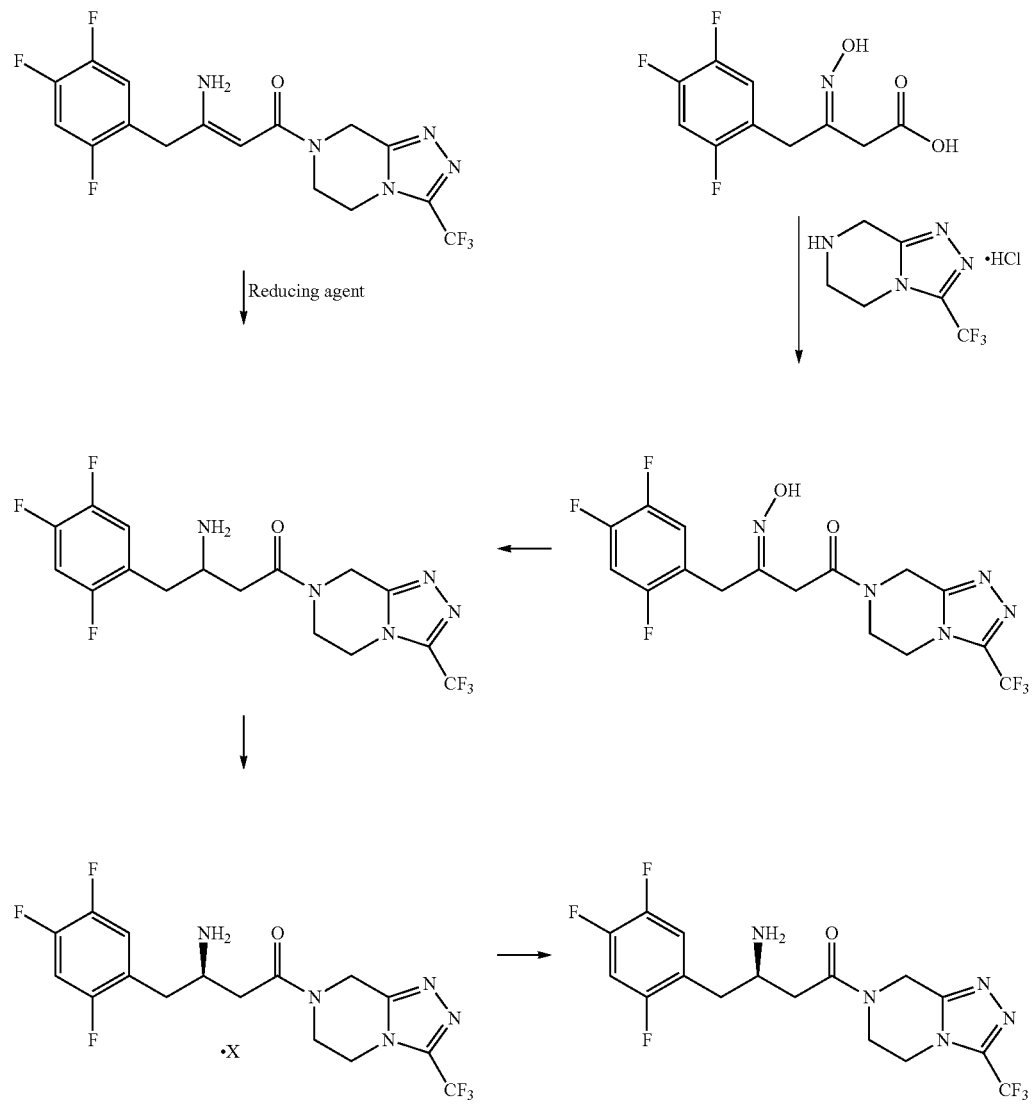

wherein X = Chiral acid

Formula I

PCT Publication No. WO 2009/085990 discloses process for the preparation of Sitagliptin by using phenylalkylamine as a chiral handle for crystallization of diastereomeric mixture as shown below:

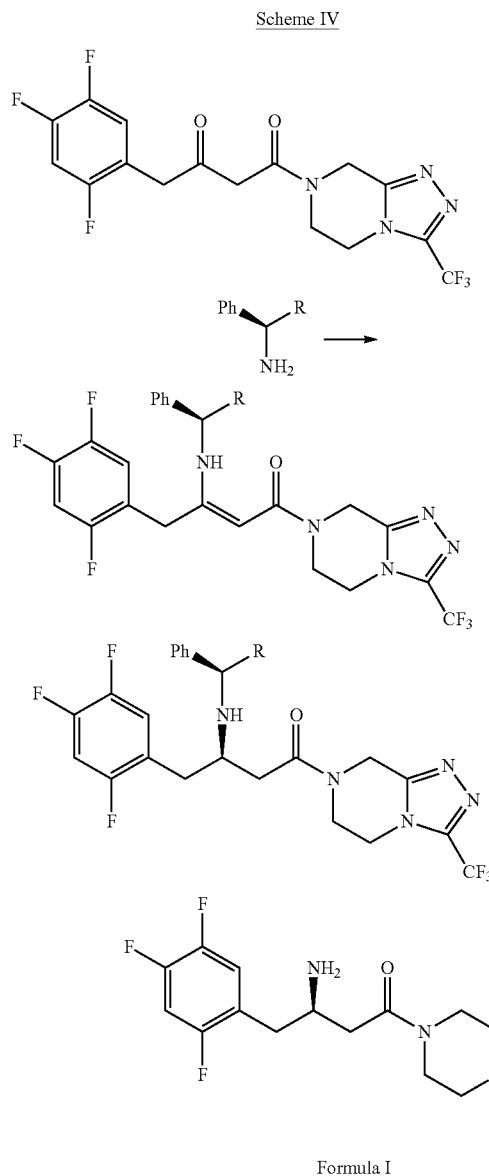

Formula I wherein R is $C_{1-4}$ alkyl

U.S. Pat. No. 8,476,437 B2 discloses the synthesis of β-amino acid derivatives and its salts by a novel process. The process comprises the reduction of a protected or unprotected prochiral β-amino acrylic acid or derivative there of, by using borane containing reducing agents at atmospheric pressure. The resulting racemic β-amino compound is resolved to a pure stereoisomer, specifically to (2R)-4-oxo-4-[3-trifluoromethyl)-5,6-dihydrol[1,2,4]triazolo[4,3-a]pyrazin-7 (8H)-yl]-1-(2,4,5-trifluorophenyl)butan-2-amine. The process is shown in the scheme given below:

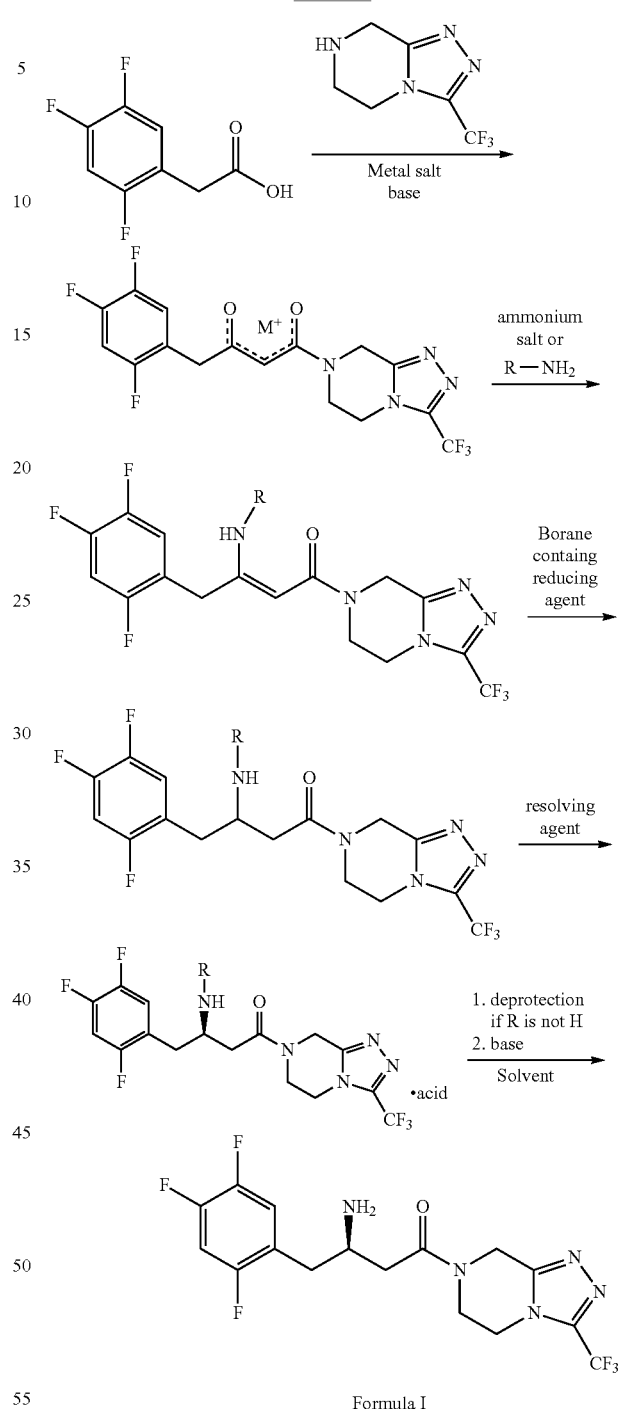

Formula I $M^+$ = Na, K, Li, Ca, Mg, Cu, Cs

R = H or protecting group

The conventional methods for the preparation of Sitagliptin are problematic in that the use of catalyst like Ru is environmentally undesirable. The other syntheses mentioned above involve expensive chiral auxiliaries for the synthesis of desired enantiomers.

In light of the evolving and more rigorous requirement demanded of drug manufacturers and the prevailing disadvantages present with known synthesis, there is a need for an improved process for the preparation of Sitagliptin and its intermediates, which circumvents the likely formation of isomeric and other process related impurities, while ensuring a target Sitagliptin with optimum yield and purity.

In addition, the processes mentioned above have disadvantages in that the preparation through racemic diastereomers gives low yield.

Therefore, there is a great need for simple, eco-friendly, convenient, inexpensive and commercially viable process for the synthesis of Sitagliptin and its intermediates or its pharmaceutically acceptable salts, which alleviate the problems associated with aforementioned process.

Objective of the Invention

The first embodiment of the present invention is to provide a novel process for the preparation of Sitagliptin Formula I.

The second embodiment of the present invention is to provide novel diastereomeric salts of racemic Sitagliptin of Formula I.

The third embodiment of the present invention is to provide a purification process of the compound of Formula I.

SUMMARY OF THE INVENTION

The present invention provides an improved process for the preparation of Sitagliptin of Formula I and its pharmaceutically acceptable salts which comprises:

i) resolving racemic Sitagliptin of Formula IV

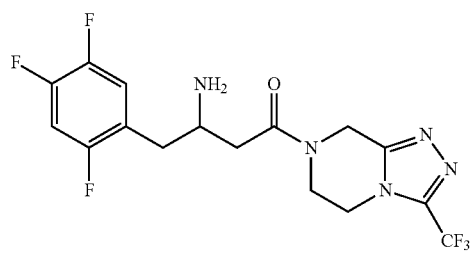
Formula IV with a chiral compound of Formula A

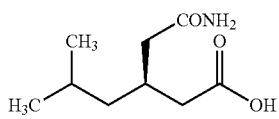
Formula A in a solvent to obtain diasteromeric salt of compound of Formula V

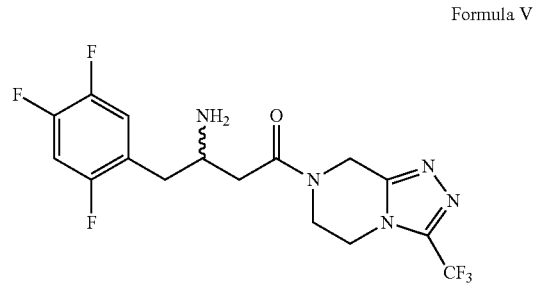
Formula V ii) converting the obtained diasteromeric salt of Formula V to compound of Formula I and its pharmaceutically acceptable salts thereof.

In one aspect, the present invention relates to a process for the preparation of compound of Formula IV

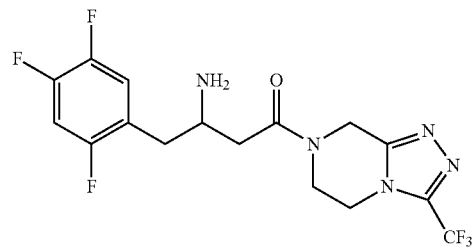
Formula IV which comprises:

i) reacting the compound of Formula II

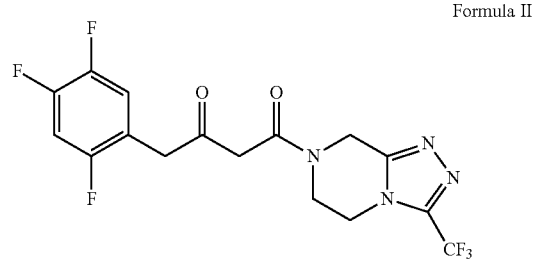 [SMILES: O=C(CC(=O)N1CCn2c(nnc2C(F)(F)F)C1)Cc1cc(F)c(F)cc1F]
Formula II with ammonia source to give compound of Formula IVa,

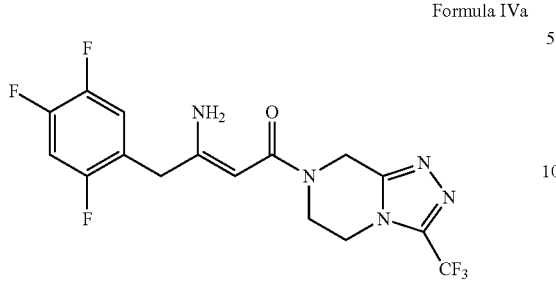
Formula IVa ii) reacting the compound of Formula IVa with formic acid to give compound of Formula IIIb

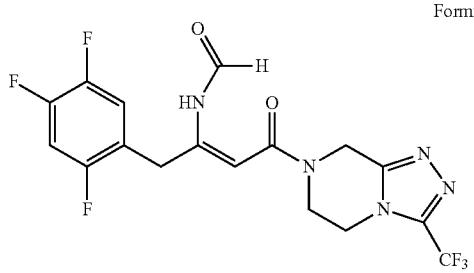
Formula IIIa iii) converting the compound of Formula IIIa to give compound of Formula IV.

In another aspect, the present invention relates to a process for the preparation of compound of Formula III

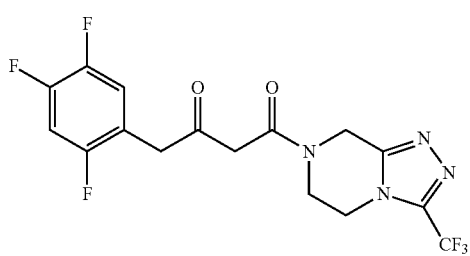
Formula III wherein X, $X^1$ represents O, S; $R^2$ represents hydrogen, alkyl which comprises reacting the compound of Formula II

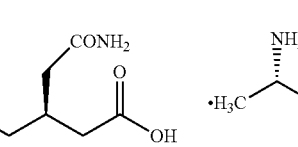
Formula II with a compound of Formula IIa

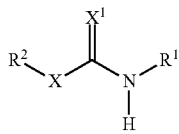
Formula IIa wherein X, $X^1$ represents O, S; $R^1$ and $R^2$ represents hydrogen or alkyl; to give compound of Formula III.

In yet another aspect, the present invention relates to a process for the preparation of compound of Formula IV by converting the compound of Formula III to give compound of Formula IV.

In yet another aspect, the present invention relates to a process for the preparation of chiral compound of Formula A

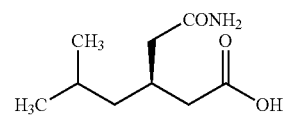

which comprises
i) resolving the racemic compound of Formula A1

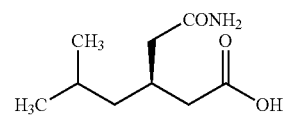
Formula A1 with (S)-(−)-phenylethylamine to give salt of the Formula B,

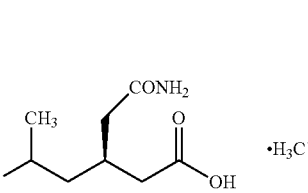
Formula B ii) converting the obtained salt of the chiral compound of Formula B to give compound of Formula A.

In another aspect, the present invention relates to a method for preparing optically substantially pure R-Sitagliptin which comprises the steps of:
i) resolving racemic Sitagliptin by precipitation with a resolving agent in the presence of a solvent,
ii) treating the recovered R-Sitagliptin salt with a base,
iii) allowing the obtained racemic Sitagliptin which is enriched in (R)-enantiomer to mix with a solvent,
iv) recovering optically substantially pure R-Sitagliptin by crystallization.

In yet another aspect, the present invention relates to a process for the preparation of racemic Sitagliptin and its further use in the present invention.
i) resolving racemic Sitagliptin with a chiral compound and obtaining a mother liquor enriched in (S)-Sitagliptin;
ii) converting (S)-Sitagliptin obtained from (i) to racemic Sitagliptin; and iii) if desired, employing racemic Sitagliptin obtained from (ii) in a process according to the present invention substantially as hereinbefore described.

In yet another aspect, the present invention relates to a novel diasteromeric salt of compound of Formula V

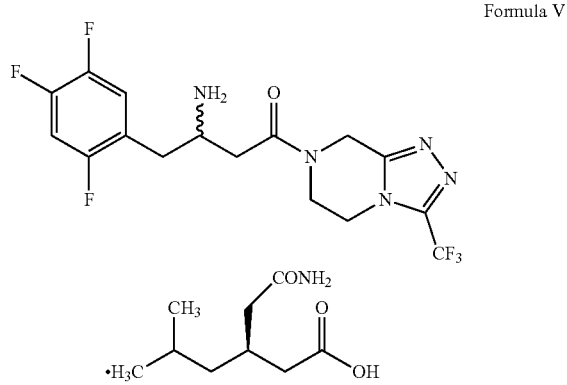

Formula V

DETAILED DESCRIPTION OF THE INVENTION

As used in the present specification, the following words and phrases are generally intended to have the meanings as set forth below, except to the extent that the context in which they are used indicates otherwise.

The present invention provides a process for the preparation of Sitagliptin of Formula I and its pharmaceutically acceptable salts thereof.

In one embodiment of the present invention the compound of Formula I and its pharmaceutically acceptable salts were prepared by first resolving the compound of Formula IV with a chiral compound in an organic solvent to obtain diasteromeric salt of Formula V. The reaction may be carried out in an organic solvent.

The organic solvent that can be used is selected from the group of alcohols such as methanol, ethanol, isopropyl alcohol and the like; ketones such as acetone, ethyl methyl ketone, methyl isobutyl ketone and the like; nitriles such as acetonitrile, propionitrile; esters such as ethyl acetate, isopropyl acetate and the like and mixtures thereof or their aqueous mixtures. Preferably the solvent used is isopropyl alcohol, ethanol, acetonitrile, ethyl acetate.

The obtained diastereomeric salt of Formula V is subsequently converted into Formula I and its pharmaceutically acceptable salts. The conversion can be carried out using an acid selected from hydrochloric acid, hydrobromic acid, sulphuric acid, nitric acid, acetic acid, methanesulfonic acid, oxalic acid, benzenesulfonic acid, para toluenesulfonic acid in a solvent selected from water, ethyl acetate, toluene, methelenedichloride and monochlorobenzene.

The chiral compound that can be used for resolution of racemic Sitagliptin is (S)-3-(2-amino-2-oxoethyl)-5-methylhexanoic acid, (1S,2S)-cyclohexane 1,2-dicarboxylicacid.

The resolution process can be carried out at temperature in the range of about 0° C. to 100° C. or reflux temperatures of the solvents. Preferably from about 20° C. to about 70° C.

In the present process of the invention one or more sequential steps are carried out without isolating intermediate compounds.

Figure 1:
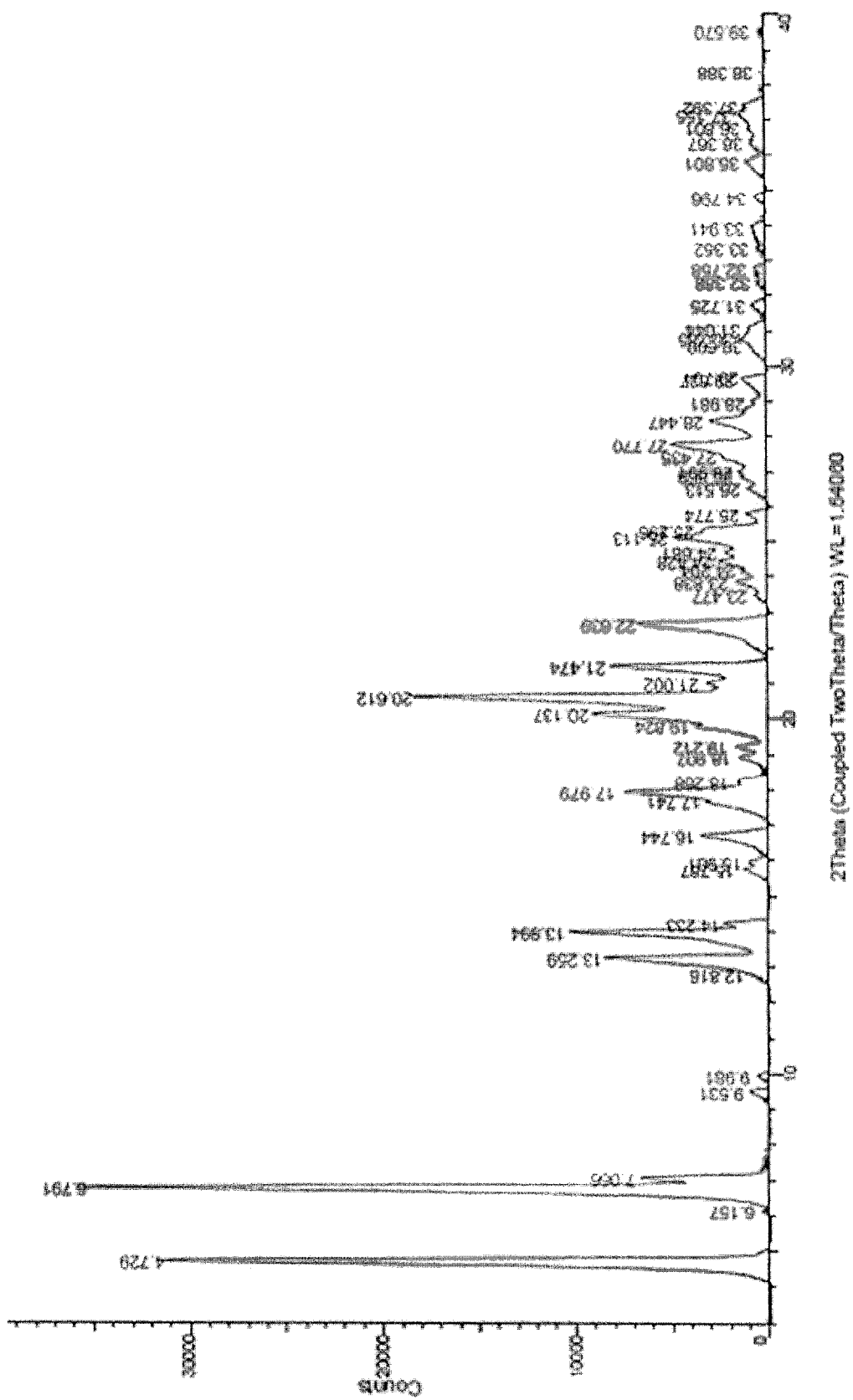
FIG. 1: Represents X-ray powder diffraction pattern of Sitagliptin acid addition salt of Formula V.

The Sitagliptin acid addition salt of Formula V obtained by the process of the present invention having an X-ray powder diffraction (XRPD) pattern with 2θ values at about 4.72, 6.79, 7.06, 13.25, 13.99, 17.97, 20.13, 20.61, 21.47, 22.63, 25.11, 27.77±0.2° which is substantially in accordance with FIG. 1.

Figure 2:
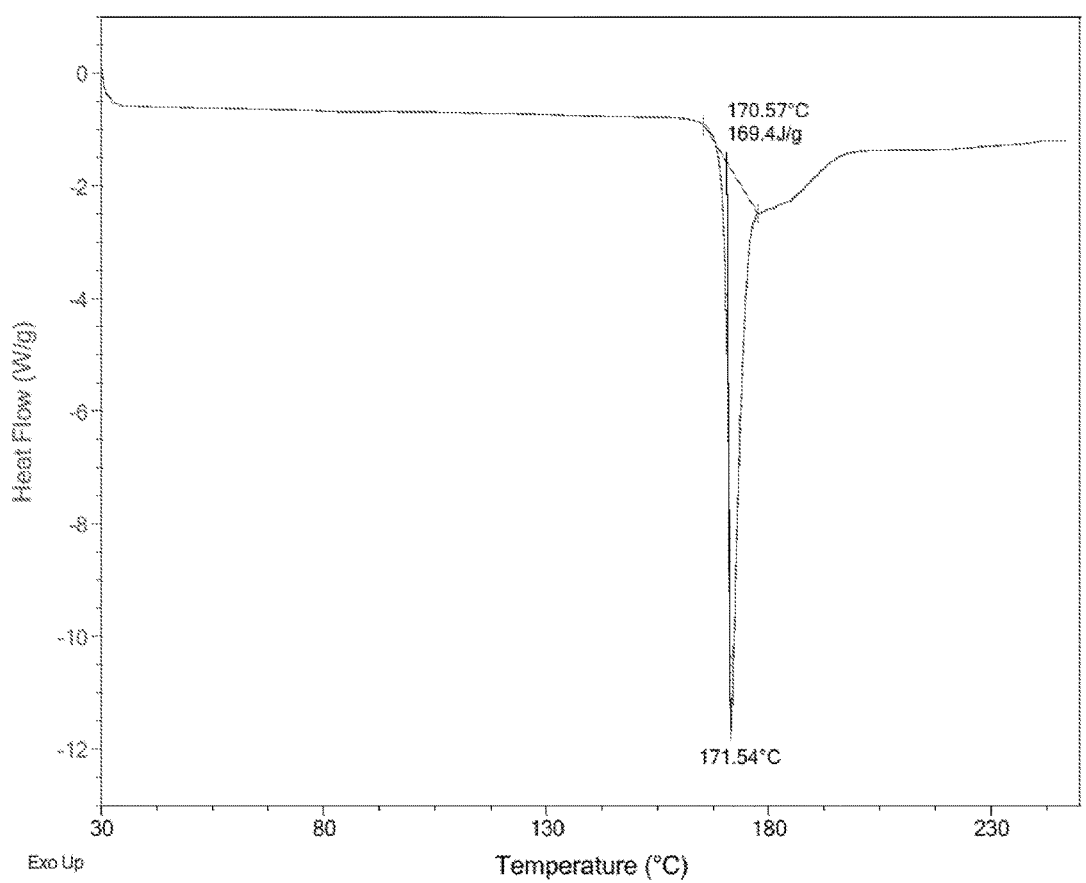
FIG. 2: Represents DSC thermogram of Sitagliptin acid addition salt of Formula V.

The Sitagliptin acid addition salt of Formula V obtained by the process of the present invention is further characterized by differential scanning calorimetry (DSC) having endothermic peak at 171.54° which is substantially in accordance with FIG. 2.

Figure 3:
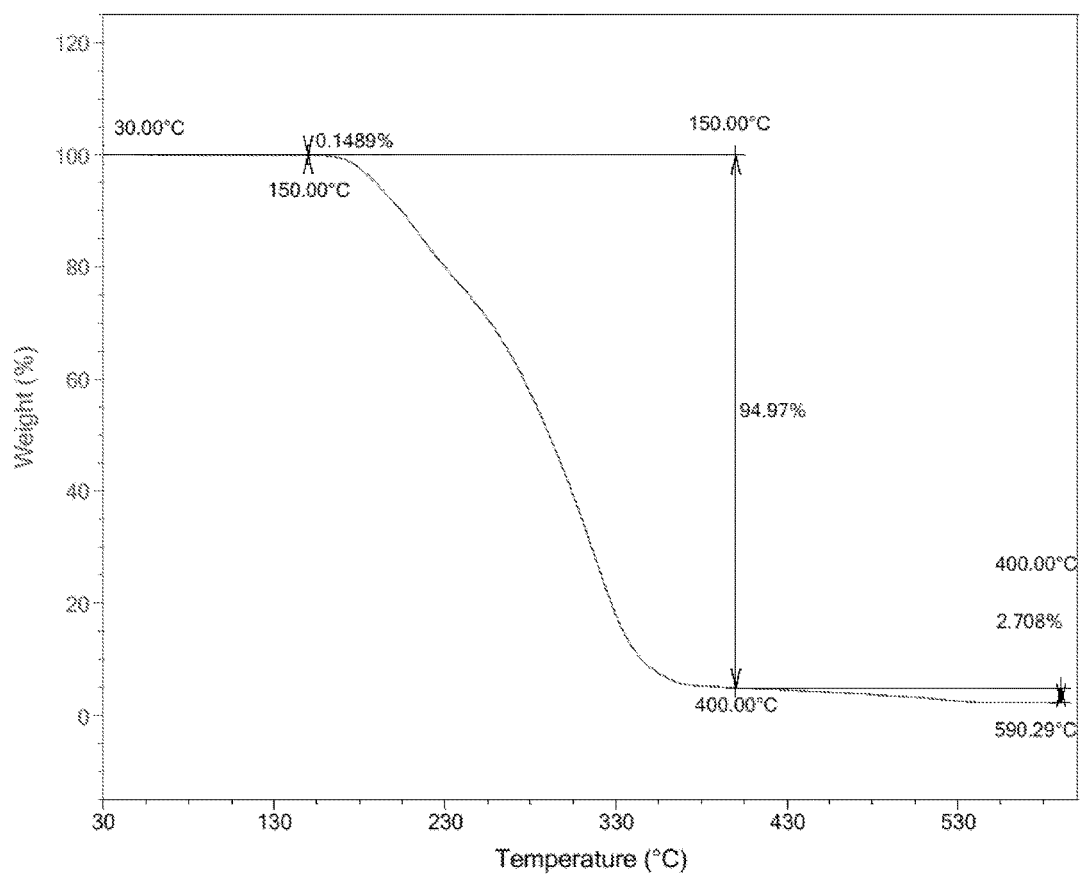
FIG. 3: Represents TGA thermogram of Sitagliptin acid addition salt of Formula V.

The Sitagliptin acid addition salt of Formula V obtained by the process of the present invention is further characterized by thermogravimetric analysis (TGA) with a weight loss of approximately 2.70% at temperatures of 150-400° C. which is substantially in accordance with FIG. 3.

In an another embodiment, suitable ammonia source used in the conversion of compound of Formula II to compound of Formula IVa is selected from anhydrous ammonia, liquid ammonia, ammonium acetate, ammonium carbonate, ammonium hydroxide, ammonium formate, ammonium lactate, ammonium citrate dibasic, ammonium carbamate, ammonium benzoate, ammonium chloride and the like.

In yet another embodiment, solvent used in the conversion of compound of Formula II to compound of Formula IVa is selected from alcohols such as methanol, ethanol, isopropyl alcohol and the like.

In yet another embodiment, the compound of Formula IIIa is converted to compound of Formula IV by conventional means. The conversion is carried out by reducing the compound of Formula IIIa using a suitable reducing agent selected from sodium borohydride, sodium cyan borohydride, sodiumtriacetoxyborohydride and the like followed by hydrolysis using base selected from sodium hydroxide, potasiumhydroxide, lithium hydroxide, calcium hydroxide in a suitable solvent selected from monochlorobenzene, toluene and ethyl acetate.

In another embodiment, the present invention relates to a process for the preparation of compound of Formula III. The compound of Formula II is reacted with compound of Formula IIa viz a carbamate in an organic solvent in the presence of a base to give compound of Formula III. The compound of Formula III is converted to compound of Formula IV by known methods in the art.

The bases employed in the condensation of compound of Formula IIa with Formula II is selected from either inorganic base like alkali metal hydroxides such as sodium hydroxide, potassium hydroxide, lithium hydroxide; alkali metal carbonates such as sodium carbonate, potassium carbonate, cesium carbonate and lithium carbonate; Alkali metal bicarbonates such as sodium bicarbonate and potassium bicarbonate; alkali metal alkoxides such as sodium methoxide, potassium methoxide, sodium tertiary butoxide, potassium tertiary butoxide or mixtures thereof or organic base selected from Triethylamine, triethanolamine, diisopropylethylamine, di-n-propylamine or mixtures thereof.

The solvent used in the reaction is selected from halogenated solvent such as dichloromethane, chloroform; ketones such as acetone; alcohol such as isopropanol; ether such as tetrahydrofuran; aprotic solvent such as dimethylformamide, N-methylpyrrolidone and the like or mixture thereof.

The organic solvents employed for the conversion of compound of Formula III to compound of Formula IV is selected from alcohols selected from methanol, ethanol, isopropyl alcohol etc.

In yet another embodiment, the present invention relates to a process for the preparation of Formula A.

In yet another embodiment, the compound of Formula A is obtained by resolving its racemate with a chiral base viz (S)-(−) phenyl ethylamine (any other resolving agents) to give compound of Formula B which is isolated a salt. The resolution is performed in solvents like alcohols such as methanol, ethanol, isopropanol, n-butanol, i-butanol, s-butanol and the like, esters such as ethyl acetate, isopropyl acetate and the like, ketones such as acetone, methylethylketone, methylisobutylketone and the like, ethers such as tetrahydrofuran, methyl-tetrahydrofuran and the like and water or mixtures thereof. The obtained salt of compound of Formula B is converted to compound of Formula A. The conversion of compound of Formula B to compound of Formula A is achieved in the presence of base selected from sodium hydroxide, potassium hydroxide, alkoxides, butoxides etc.

In another embodiment, the mother liquor from resolution step or the mother liquor from each recrystallization, is enriched with (S)-Sitagliptin. (S)-Sitagliptin present in one or more of these liquors, or the pooled liquors, may be converted into racemic Sitagliptin for reuse in a process according to the present invention substantially as hereinbefore described.

Suitably, one or more mother liquors obtained from the process as described above, or pooled such mother liquors, may be treated with a base to remove any residual chiral acid and to thereby afford the free base enriched in (S)-Sitagliptin. The free base can then be converted to the racemate, typically by reflux in a suitable solvent for several hours, optionally in the presence of a suitable acid for example HCl or a base for examples NaOH, which racemate can then be recycled for use in a process according to the present invention.

The Sitagliptin prepared by the above methods can also be converted into its pharmaceutically acceptable salts such as phosphate, hydrochloride and the like, preferably phosphate which is shown below:

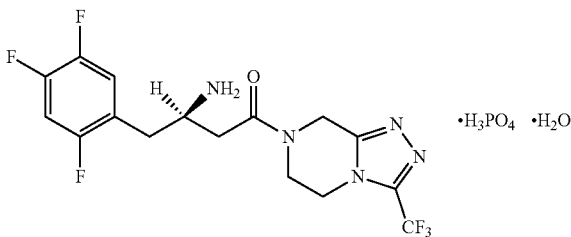 [SMILES: N[C@@H](CC(=O)N1CCn2c(nnc2C(F)(F)F)C1)Cc1cc(F)c(F)cc1F ; "·H3PO4" ; O]

The process briefly involves reacting a pharmaceutically acceptable salt with Sitagliptin in solution.

R-Sitagliptin or any pharmaceutically acceptable salts of R-Sitagliptin prepared in accordance with the present invention contains less than about 0.5%, of the corresponding impurities as characterized by a chiral HPLC (high performance liquid chromatography) chromatogram obtained from a mixture comprising the desired compound and one or more of the said impurities, preferably less than about 0.1%.

The percentage here refers to weight percent obtained from the area-% of the peaks representing the impurities. R-Sitagliptin and salts thereof also are substantially free of other process-related impurities.

The process of the present invention advantageously provides R-Sitagliptin or its pharmaceutically acceptable salts in relatively high purity, e.g., greater than about 98% ee and preferably greater than about 99%.

The R-Sitagliptin or its pharmaceutically acceptable salts obtained by the processes of the present invention has residual organic solvent less than the amount recommended for pharmaceutical products, as set forth for example in ICH guidelines and U.S. Pharmacopoeia; the recommended amount is less than 5000 ppm for methanol, ethyl acetate and acetone; less than 800 ppm for toluene, dichloromethane, dimethylformamide and Diisopropyl ether. Preferably, the amount is less than about 5000 ppm residual organic solvent, preferably, more preferably less than about 2000 ppm residual organic solvent, most preferably, less than about 700 ppm.

It will be understood that various modifications may be made to the embodiments disclosed herein. Therefore, the above description should not be construed as limiting, but merely as exemplifications of preferred embodiments. The present invention is exemplified by the following example, which is provided for illustration only and should not be construed to limit the scope of the invention.

The following examples describes the nature of the invention and are given only for the purpose of illustrating the present invention in more detail and are not limitative and relate to solutions which have been particularly effective on a bench scale.

EXAMPLES

Example 1

Preparation of (Z)-3-amino-1-(3-(trifluoromethyl)-5, 6-dihydro-[1,2,4]triazolo[4,3-a]pyrazin-7(8H)-yl)-4-(2,4,5-trifluorophenyl)but-2-en-1-one To the mixture of 4-oxo-4-[3-(trifluoromethyl)-5,6-dihydro[1,2,4]triazolo[4,3,-a]pyrazin-7(8H)-yl]-1-(2,4,5-trifluorophenyl)butan-2-one (427.0 g) (prepared as per U.S. Pat. No. 7,326,708 B2 (or) J. Am. Chem. Soc. 2009, 131, 8798-8804) and methanol (1000 ml) was purged dry ammonia gas (53.6 g) at 25-30° C., heated to reflux (60-65° C.) and maintained the reaction mass at the same temperature for about 3.0-4.0 hrs. Cooled the reaction mass to 0-5° C., filtered the precipitated solid and washed with chilled methanol. Dried the wet cake at 60-65° C. to obtain 340.0 g of the title compound. Molar yield 79.8%; purity by HPLC: 98.99%.

Example 2

Preparation of (R)-3-amino-1-(3-(trifluoromethyl)-5, 6-dihydro-[1,2,4]triazolo[4,3-a]pyrazin-7 (8H)-yl)-4-(2,4,5-trifluorophenyl)butan-1-one (S)-3-(2-amino-2-oxoethyl)-5-methyl hexanoate (Sitagliptin Diastereomeric Salt)

Mixture of (Z)-3-amino-1-(3-(trifluoromethyl)-5,6-dihydro-[1,2,4]triazolo[4,3-a]pyrazin-7(8H)-yl)-4-(2,4,5-trifluorophenyl)but-2-en-1-one (100.0 g) and Monochlorobenzene (750.0 ml) was cooled to 0-5° C. Sodium borohydride (24.4 g; 2.66 eq) followed by formic acid (330.0 ml; 35.5 eq) was added to the reaction mass at 0-5° C. and maintained the reaction mass until the completion of the reaction i.e, until the TLC complies at the same temperature. Water (1600.0 ml) was added after TLC complies and raised the temperature of the reaction mass to 50-55° C. Separated the aqueous & organic layers and washed the aqueous layer with Monochlorobenzene (200 ml). To the aqueous layer Methelenedichloride (300 ml) was added and adjusted the pH of the reaction mass to 10-11 with 48% caustic lye. Separated the aqueous & organic layers and extracted the aqueous layer with Methelenedichloride (MDC). Combined all the organic layers and washed with 20% sodium chloride solution, followed by water. Distilled off the Organic layer and co-distilled with isopropyl alcohol (100.0 ml). To the obtained racemic Sitagliptin crude was added isopropyl alcohol (500.0 ml) and (S)-3-(2-amino-2-oxoethyl)-5-methylhexanoicacid (28.0 g), heated the mixture to reflux and slowly cooled to room temperature. Filtered the precipitated solid and washed with Isopropyl alcohol (100.0 ml). To the wet cake isopropyl alcohol (200.0 ml) was added and heated to reflux. Cooled the reaction mixture to room temperature filtered the product and washed with isopropyl alcohol (75.0 ml). The wet cake was dried under vacuum at 50-55° C. to obtain 57.0 g of Sitagliptin diastereomeric salt. Molar yield: 38.7%; Chiral HPLC: Desired product: 99.78%; Isomer: 0.22%, Purity by HPLC>99.0%; SOR: −20.0°; Melting range: 168-172° C.

Example 3

Preparation of (R)-3-amino-1-(3-(trifluoromethyl)-5, 6-dihydro-[1,2,4]triazolo[4,3-a]pyrazin-7(8H)-yl)-4-(2,4,5-trifluorophenyl)butan-1-one (S)-3-(2-amino-2-oxoethyl)-5-methyl Hexanoate (Sitagliptin Diastereomeric Salt)

Mixture of (Z)-3-amino-1-(3-(trifluoromethyl)-5,6-dihydro-[1,2,4]triazolo[4,3-a]pyrazin-7(8H)-yl)-4-(2,4,5-trifluorophenyl)but-2-en-1-one (100.0 g), acetonitrile (50.0 ml) and Monochlorobenzene (300.0 ml) was cooled to 10-15° C. Sodium borohydride (18.6 g; 2.0 eq) followed by formic acid (111.5 ml; 12.0 eq) was added to the reaction mass at 10-15° C. and maintained the reaction mass until the completion of the reaction i.e, until the TLC complies at the same temperature. Water (1200.0 ml) was added after TLC complies and raised the temperature of the reaction mass to 50-55° C. Separated the aqueous & organic layers and washed the aqueous layer with Monochlorobenzene (300 ml). To the aqueous layer Methelenedichloride (300 ml) was added and adjusted the pH of the reaction mass to 10-11 with caustic lye. Separated the aqueous & organic layers and extracted the aqueous layer with Methelenedichloride. Combined all the organic layers and washed with 20% sodium chloride solution, followed by water. Distilled off the Organic layer and co-distilled with isopropyl alcohol (100.0 ml). To the obtained racemic Sitagliptin crude was added isopropyl alcohol (500.0 ml) and (S)-3-(2-amino-2-oxoethyl)-5-methylhexanoicacid (28.0 g), heated the mixture to reflux and slowly cooled to room temperature. Filtered the precipitated solid and washed with Isopropyl alcohol (100.0 ml). To the wet cake isopropyl alcohol (200.0 ml) was added and heated to reflux. Cooled the reaction mixture to room temperature filtered the product and washed with isopropyl alcohol (75.0 ml). The wet cake was dried under vacuum at 50-55° C. to obtain 54.5 g of Sitagliptin diastereomeric salt. Molar yield: 37.4%; Chiral HPLC: Desired product: 99.37%; Isomer: 0.63%, Purity by HPLC>99.0%; SOR: −20.0°; Melting range: 168-172° C.

Example 4

Preparation of (R)-3-amino-1-(3-(trifluoromethyl)-5, 6-dihydro-[1,2,4]triazolo[4,3-a]pyrazin-7(8H)-yl)-4-(2,4,5-trifluorophenyl)butan-1-one (S)-3-(2-amino-2-oxoethyl)-5-methylhexanoate (Sitagliptin Diastereomeric Salt)

Mixture of racemic Sitagliptin (50.0 g), Isopropyl alcohol (250.0 ml) and 0.6 equivalent of (S)-3-(2-amino-2-oxoethyl)-5-methylhexanoicacid were heated to reflux and cooled to room temperature. Filtered the precipitated solid and washed with isopropyl alcohol. To the wet cake 3.0 volumes of isopropyl alcohol was added, heated to reflux and cooled to room temperature. Filtered the precipitated solids, washed with isopropyl alcohol and dried to give 26.0 g of the title compound; yield 35.6%; SOR: −20.0°; chiral HPLC: 99.4%; isomer: 0.6%, Melting range: 168-172° C.

Example 5

Preparation of (R)-3-amino-1-(3-(trifluoromethyl)-5, 6-dihydro-[1,2,4]triazolo[4,3-a]pyrazin-7 (8H)-yl)-4-(2,4,5-trifluorophenyl)butan-1-one (S)-3-(2-amino-2-oxoethyl)-5-methylhexanoate (Sitagliptin Diastereomeric Salt)

Mixture of racemic Sitagliptin (25.0 g), ethanol (75.0 ml) and 0.6 equivalent of (S)-3-(2-amino-2-oxoethyl)-5-methylhexanoicacid were heated to reflux and cooled to room temperature. Filtered the precipitated solid and washed with ethanol. To the wet cake 3.0 volumes of ethanol was added, heated to reflux and cooled to room temperature. Filtered the precipitated solids, washed with ethanol and dried to give 10.0 g of the title compound; yield 27.4%; SOR: −19.8°; chiral HPLC: 99.68%; isomer: 0.32%; Melting range: 168-171° C.

Example 6

Preparation of (R)-3-amino-1-(3-(trifluoromethyl)-5, 6-dihydro-[1,2,4]triazolo[4,3-a]pyrazin-7 (8H)-yl)-4-(2,4,5-trifluorophenyl)butan-1-one (S)-3-(2-amino-2-oxoethyl)-5-methylhexanoate (Sitagliptin Diasteromeric Salt)

Mixture of racemic Sitagliptin (25.0 g), acetonitrile (75.0 ml) and 0.6 equivalent of (S)-3-(2-amino-2-oxoethyl)-5-methylhexanoicacid were heated to reflux and cooled to room temperature. Filtered the precipitated solid and washed with acetonitrile. To the wet cake 3.0 volumes of acetonitrile was added, heated to reflux and cooled to room temperature. Filtered the precipitated solids, washed with acetonitrile and dried to give 14.0 g of the title compound; yield 38.4%; SOR: −19.90°; chiral HPLC: 99.4%, isomer: 0.6%, Melting range: 168.2-169.9° C.

Example 7

Preparation of (R)-3-amino-1-(3-(trifluoromethyl)-5, 6-dihydro-[1,2,4]triazolo[4,3-a]pyrazin-7(8H)-yl)-4-(2,4,5-trifluorophenyl)butan-1-one (S)-3-(2-amino-2-oxoethyl)-5-methylhexanoate (Sitagliptin Diastereomeric Salt)

Mixture of racemic Sitagliptin (25.0 g), ethyl acetate (200.0 ml) and 0.6 equivalent of (S)-3-(2-amino-2-oxoethyl)-5-methylhexanoicacid were heated to reflux and cooled to room temperature. Filtered the precipitated solid and washed with ethyl acetate. To the wet cake 3.0 volumes of ethyl acetate was added, heated to reflux and cooled to room temperature. Filtered the precipitated solids, washed with ethyl acetate and dried to give 15.0 g of the title compound; yield 41.1%; SOR: −18.5°; chiral HPLC: 95.6%; isomer: 4.4%; Melting range: 166.5-167.8° C.

Example 8

Preparation of 7-[(3R)-3-amino-1-oxo-4-(2, 4, 5-fluorophenyl) butyl]5, 6, 7, 8-tetrahydro-3-(trifluoromethyl)-1,2,4-triazolo[4,3,a]pyrazine phosphate(1:1)monohydrate (Sitagliptin Phosphate Monohydrate)

Mixture of diastereomeric salt of Sitagliptin (30.0 g) and DM water (60.0 ml) were cooled and acidified with hydrochloric acid. Filtered the solids and (S)-3-(2-amino-2-oxoethyl)-5-methylhexanoate was recovered. Adjusted the pH of the reaction mass to 10-11 with sodium carbonate solution and extracted the product with methylene dichloride (120 ml). Washed the organic layer with water and distilled off the solvent. To the residue (syrupy liquid) thus obtained was added isopropyl alcohol (15.0 ml) and co-distilled to remove traces of MDC. To the residue thus obtained was added isopropyl alcohol (100.0 ml), stirred and filtered the solution. Orthophosphoricacid (7.0 g) was added to the filtrate at room temperature and then heated to reflux temperature. Stirred for about 15 minutes and DM water (32.0 ml) was added slowly at reflux temperature. Cooled the reaction mixture to 30° C. for about 2.0 hrs, further cooled to 0-5° C. and stirred for about 30 min. Filtered the precipitated solid, washed with isopropyl alcohol (15 ml) and dried the product at 55-60° C. to give 19.0 g of Sitagliptin phosphate monohydrate; yield 71.8%; M.R: 204-205° C.; SOR: −21.8°, Chiral HPLC: 99.88%, Isomer: 0.12%: Purity by HPLC: 99.93%.

Example 9

Preparation of 7-[(3R)-3-amino-1-oxo-4-(2, 4, 5-fluorophenyl) butyl]5, 6, 7, 8-tetrahydro-3-(trifluoromethyl)-1,2,4-triazolo[4,3,a]pyrazinephosphate (1:1)monohydrate (Sitagliptin Phosphate Monohydrate)

Mixture of diastereomeric salt of Sitagliptin (100.0 g) and DM water (300.0 ml) were cooled and acidified with hydrochloric acid. Filtered the solids, washed with DM water and (S)-3-(2-amino-2-oxoethyl)-5-methylhexanoate (70-80%) was recovered by drying the wet cake. Adjusted the pH of the reaction mass to 9.0-10 with sodium carbonate solution and extracted the product with 2×100 ml of methylene dichloride. Washed organic layer with water and distilled off the solvent. To the residue (syrupy liquid) thus obtained was added ethyl acetate (100.0 ml) and co-distilled to remove traces of MDC. To the residue thus obtained was added ethyl acetate (300.0 ml), stirred and filtered the solution. DM water (100 ml) and orthophosphoricacid (23.3.0 g) was added to the filtrate at room temperature and then heated to reflux temperature. Stirred for about 15 minutes and DM water (32.0 ml) was added slowly at reflux temperature. Cooled the reaction mixture to 30° C. for about 2.0 hrs, further cooled to 0-5° C., Sitagliptin.H$_3$PO$_4$.H$_2$O seeding (1.0 g) was added to the reaction mass and stirred for about 2-3 hours. Filtered the precipitated solid, washed with ethyl acetate (100 ml) and dried the product at 35-40° C. to give 70.0 g of Sitagliptin phosphate monohydrate; yield 79.5%; M.R: 204-206° C.; SOR: −21.04° C.=1, in Water, Purity by Chiral HPLC: 99.92%; isomer content: 0.08%; Purity by HPLC: 99.89%.

We claim:

1. A Sitagliptin acid addition salt of Formula V

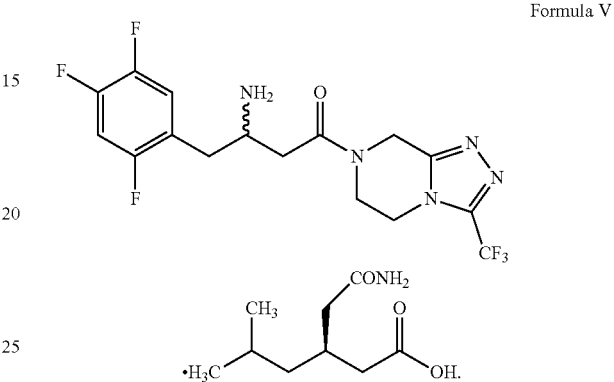

Formula V

2. The Sitagliptin acid addition salt according to claim 1, being in crystalline form and having a powder X-ray diffraction pattern comprising the following characteristic reflection angles 2θ at about 4.72, 6.79, 7.06, 13.25, 13.99, 17.97, 20.13, 20.61, 21.47, 22.63, 25.11, 27.77±0.2°.

3. The Sitagliptin acid addition salt according to claim 1, characterized by differential scanning calorimetry (DSC) thermogram having endothermic peak at 171.54°.

4. The Sitagliptin acid addition salt according to claim 1, further characterized by thermogravimetric analysis (TGA) with a weight loss of approximately 2.70% at temperatures of 150-400° C.

5. A process for the preparation of Sitagliptin acid addition salt of Formula V, comprising:

resolving racemic Sitagliptin of Formula IV

Formula IV with a chiral compound of Formula A

Formula A in a solvent to obtain diasteromeric salt of compound of Formula V

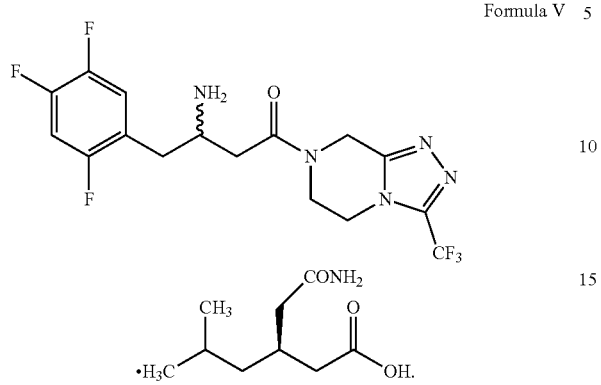

Formula V

6. The process of claim 5, further comprising converting the obtained diasteromeric salt of Formula V to compound of Formula I

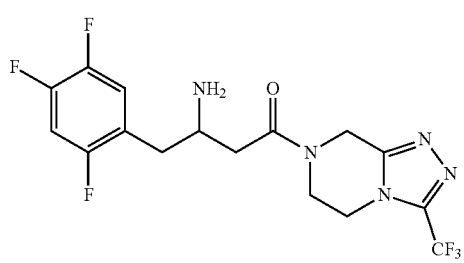

Formula I or its pharmaceutically acceptable salts thereof.

7. The process according to claim 5, wherein the solvent used for resolution is selected from methanol, ethanol, isopropyl alcohol, acetone, ethyl methyl ketone, methyl isobutyl ketone, acetonitrile, propionitrile, ethyl acetate, isopropyl acetate and mixtures thereof.

8. The process according to claim 6, wherein converting is carried out using an acid selected from hydrochloric acid, hydrobromic acid, sulphuric acid, nitric acid, acetic acid, methanesulfonic acid, oxalic acid, benzenesulfonic acid, para toluenesulfonic acid in a solvent selected from water, ethyl acetate, toluene, methelenedichloride or monochlorobenzene.

9. A process for the preparation of compound of Formula IV

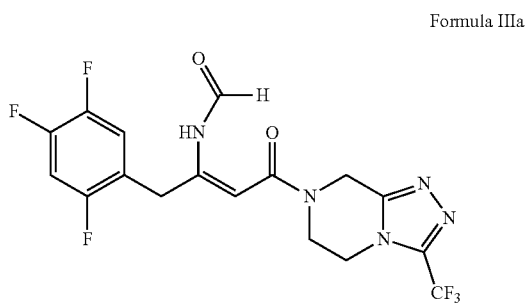 [SMILES: O=CN/C(=C\C(=O)N1CCn2c(nnc2C(F)(F)F)C1)Cc1cc(F)c(F)cc1F]

Formula IV which comprises:

step (i): reacting the compound of Formula II

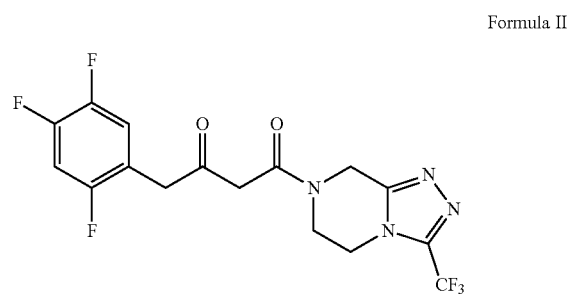 [SMILES: O=C(CC(=O)N1CCn2c(nnc2C(F)(F)F)C1)Cc1cc(F)c(F)cc1F]

Formula II with ammonia source to give compound of Formula IVa,

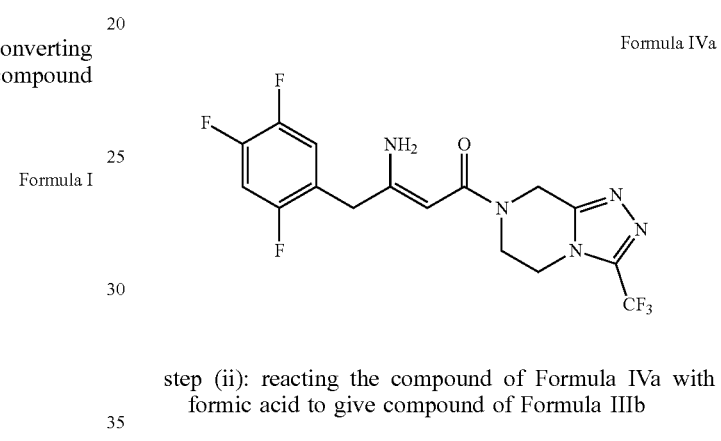

Formula IVa step (ii): reacting the compound of Formula IVa with formic acid to give compound of Formula IIIb Formula IIIa step (iii): converting the compound of Formula IIIa to give compound of Formula IV.

10. The process according to claim 9, wherein the ammonia source used in step (i) is selected from anhydrous ammonia, liquid ammonia, ammonium acetate, ammonium carbonate, ammonium hydroxide, ammonium formate, ammonium lactate, ammonium citrate dibasic, ammonium carbamate, ammonium benzoate, and ammonium chloride.

11. The process according to claim 9, wherein the solvent used in step (i) is selected from methanol, ethanol, and isopropyl alcohol.

12. The process according to claim 9, wherein the conversion in step (iii) is carried out by reducing the compound of Formula IIIa using a suitable reducing agent selected from sodium borohydride, sodium cyanoborohydride or sodium triacetoxyborohydride followed by hydrolysis using base selected from sodium hydroxide, potassiumhydroxide, lithium hydroxide, calcium hydroxide in a suitable solvent selected from monochlorobenzene, toluene and ethyl acetate.

13. A process for the preparation of compound of Formula III

Formula III

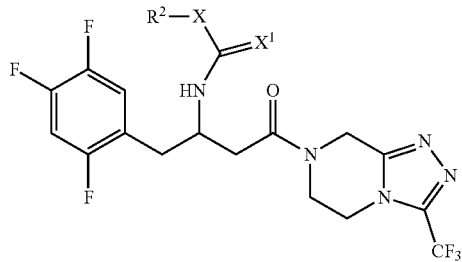

wherein X, X$^1$ represents O, S; R$^2$ represents hydrogen, alkyl
which comprises reacting the compound of Formula II Formula II

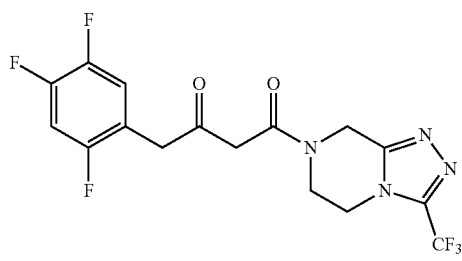

with a compound of Formula IIa

Formula IIa

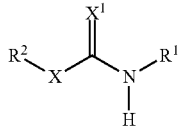

wherein X, X$^1$ represents O, S; R$^1$ and R$^2$ represents hydrogen or alkyl; to give compound of Formula III, wherein the reaction is carried out in a suitable solvent in the presence of a base.

14. The process according to claim 13, wherein the base is inorganic base selected from sodium hydroxide, potassium hydroxide, lithium hydroxide, sodium carbonate, potassium carbonate, cesium carbonate, lithium carbonate, sodium bicarbonate, potassium bicarbonate, sodium methoxide, potassium methoxide, sodium tertiary butoxide, potassium tertiary butoxide, and mixtures thereof.

15. The process according to claim 13, wherein the solvent used in the reaction is selected from dichloromethane, chloroform, acetone, isopropanol, tetrahydrofuran, dimethylformamide, N-methylpyrrolidone or mixtures thereof.

16. The process according to claim 13, wherein the base is organic base selected from the group of organic bases consisting of triethylamine, triethanolamine, diisopropylethylamine, di-n-propylamine and mixtures thereof.

* * * * *